US010016357B2

(12) United States Patent
Rivers, IV et al.

(10) Patent No.: US 10,016,357 B2
(45) Date of Patent: Jul. 10, 2018

(54) PERSONAL LUBRICANTS

(71) Applicant: Nature Labs USA LLC, Medford, NJ (US)

(72) Inventors: Louis J. Rivers, IV, Medford, NJ (US); Kevin Stranen, Media, PA (US)

(73) Assignee: THE BEAUTY FACTORY, LLC, Bridgeton, NJ (US)

( * ) Notice: Subject to any disclaimer, the term of this patent is extended or adjusted under 35 U.S.C. 154(b) by 660 days.

(21) Appl. No.: 13/849,000

(22) Filed: Mar. 22, 2013

(65) Prior Publication Data

US 2013/0251818 A1    Sep. 26, 2013

Related U.S. Application Data

(60) Provisional application No. 61/614,139, filed on Mar. 22, 2012.

(51) Int. Cl.

| *A61K 36/00* | (2006.01) |
|---|---|
| *A61K 9/00* | (2006.01) |
| *A61K 35/644* | (2015.01) |
| *A61K 31/047* | (2006.01) |
| *A61K 45/06* | (2006.01) |
| *A61K 47/02* | (2006.01) |
| *A61K 31/198* | (2006.01) |
| *A61K 35/64* | (2015.01) |

(52) U.S. Cl.
CPC .......... *A61K 9/0034* (2013.01); *A61K 31/047* (2013.01); *A61K 31/198* (2013.01); *A61K 35/644* (2013.01); *A61K 45/06* (2013.01); *A61K 47/02* (2013.01)

(58) Field of Classification Search
CPC ....................................................... A61K 36/00
USPC ........................................................ 424/725
See application file for complete search history.

(56) References Cited

U.S. PATENT DOCUMENTS

| 5,534,505 A * | 7/1996 | Widauer ............. A61K 31/575 |
|---|---|---|
| | | 514/169 |
| 5,871,754 A | 2/1999 | Briggs et al. ................. 424/401 |
| 6,632,445 B2 * | 10/2003 | Richardson .......... A61K 9/0034 |
| | | 424/204.1 |
| 8,187,659 B2 * | 5/2012 | Robertson ................ A61K 9/08 |
| | | 106/162.1 |
| 2007/0071694 A1* | 3/2007 | Shizukuishi ............. C07K 7/06 |
| | | 424/50 |
| 2007/0238071 A1* | 10/2007 | Wagner ................. A61K 8/345 |
| | | 433/216 |
| 2008/0057089 A1 | 3/2008 | Molina ......................... 424/401 |
| 2008/0131561 A1* | 6/2008 | Patanawongyuneyong ............... |
| | | A23L 1/0532 |
| | | 426/72 |
| 2008/0193489 A1* | 8/2008 | De Armond ......... A61K 9/0014 |
| | | 424/400 |
| 2011/0015481 A1 | 1/2011 | Scala ............................. 600/38 |

FOREIGN PATENT DOCUMENTS

EP         1050295 A1 *  11/2000   ............... A61K 8/24

* cited by examiner

*Primary Examiner* — Christopher R Tate
*Assistant Examiner* — Deborah A Davis
(74) *Attorney, Agent, or Firm* — Licata & Tyrrell P.C.

(57) ABSTRACT

Personal lubricants containing royal jelly, a glow powder or xylitol are provided.

5 Claims, No Drawings

PERSONAL LUBRICANTS

This patent application claims the benefit of priority from U.S. Provisional Patent Application Ser. No. 61/614,139, filed Mar. 22, 2012, the teachings of which are herein incorporated by reference in their entirety.

FIELD OF THE INVENTION

The present invention relates to personal lubricants containing royal jelly or a glow powder or xylitol.

BACKGROUND OF THE INVENTION

Royal jelly is a honey bee secretion that is used in the nutrition of larvae, as well as adult queens. Royal jelly is collected and sold as a dietary supplement for humans, claiming various health benefits because of components such as B-complex vitamins such as pantothenic acid (vitamin $B_5$) and vitamin $B_6$ (pyridoxine). Royal jelly is used as a component in some skin care and natural beauty products. See, for example, U.S. Pat. No. 5,871,754 discloses a make-up composition in the form of water-in-oil or oil-in-water emulsion which may contain as one of its components royal jelly.

Published U.S. Patent Application No. 2008/0057089 discloses a light emitting personal lubricant with a light emitting pigment.

Xylitol $((CHOH)_3(CH_2OH)_2)$ is an achiral isomer of pentane-1,2,3,4,5-pentol which can function as a diabetic sweetener and which is actively beneficial for dental health and has been shown to reduce the incidence of acute middle ear infections. Published U.S. Patent Application No. 20110015481 discloses a sexual enhancement lubrication powder wherein xylitol can be included as a sialogogue/sweetener. Published U.S. Patent Application No. 2008/0193489 discloses and claims a personal lubricant composition, comprising at least 1% xylitol, wherein the formulation is free of preservatives and glycerin.

SUMMARY OF THE INVENTION

An aspect of the present invention relates to a personal lubricant comprising royal jelly.

Another aspect of the present invention relates to a personal lubricant comprising a glow powder.

Another aspect of the present invention relates to a personal lubricant comprising xylitol.

DETAILED DESCRIPTION OF THE INVENTION

Provided by the present invention are personal lubricants.

In one embodiment, the personal lubricant comprises the honey bee secretion known as royal jelly. In one embodiment, the royal jelly is included in the personal lubricant at a percentage of about 0.001% by volume of the formula. A nonlimiting example of a commercial supplier of the royal jelly is beehoney with the extension .com/royaljelly.html of the world wide web.

In this embodiment, the lubricant further comprises one or more additional components known by those of skill in the art to be useful in personal lubricants. For example, in one embodiment, the personal lubricant may further comprise a component which provides lubricity and/or serves as a thickening agent. Examples include, but are not limited to carrageenan, glycerin, propylene glycol, polyquaternium, methylparaben, propylparaben, cellulose polymer, cyclomethicone, dimethicone, dimethiconol, petroleum based oils, plant based oils, as well as other substances that reduce the coefficient of friction or increases lubricity of the final formula, and mixtures thereof. In one embodiment, the component which provides lubricity and/or serves as thickening agent is carrageenan. In addition to providing lubricity and serving as a thickening agent, carrageenan also has no taste, no smell, no color, allows for moisture retention, has pseudoplastic properties, acts as an emulsifier and has been shown to offer protection against human papillomavirus in previous clinical trials and may also offer some protection against HSV-2, the virus that causes herpes. In one embodiment, carrageenan is added in an amount of about 0.75% by volume to the formula. A nonlimiting example of a commercial supplier is Tedson Additive Inc.

In another embodiment, the personal lubricant may further comprise a thickening agent such as, but not limited to a plant based gum such as hydroxyethyl cellulose gum. Plant based gums serve to thicken the formula and prevent separation of the various ingredients of the formulation. In one embodiment, hydroethyl cellulose gum is added in an amount of about 0.7% by volume to the formula. A nonlimiting example of a commercial supplier is Tedson Additive Inc.

In another embodiment, the personal lubricant may further comprise a Lewis acid for adjustment of the pH. Examples include, but are not limited to, citric acid, phosphoric acid, hydrochloric acid, ascorbic acid, malic acid and lactic acid.

In another embodiment, the personal lubricant may further comprise an antiviral component such as L-lysine HCl. Viruses such as HSV are dependent on the presence of L-arginine to replicate. By flooding the virus with L-lysine, the opposing amino acid, it helps to stop the replication of the virus. In one embodiment, the L-lysine HCL is included in the personal lubricant at a percentage of about 0.001% by volume of the formula.

In another embodiment, the personal lubricant may further comprise a preservative such as sodium benzoate or potassium benzoate. In one embodiment, the preservative is also bacteriostatic and fungistatic under acidic conditions. In one embodiment, the preservative is included in the personal lubricant at a percentage of about 0.01% or less by volume of the formula.

In yet another embodiment, the personal lubricant may further comprise an agent which inhibits molds and yeasts such as, but not limited to, potassium sorbate, sodium sorbate or xylitol. In one embodiment, the inhibitor of molds and yeasts is included in the personal lubricant at a percentage of about 0.05% to 0.3% by volume of the formula.

In one embodiment of the present invention, the personal lubricant comprises royal jelly, carrageenan, hydroxyethyl cellulose gum, citric acid, L-lysine HCl, sodium benzoate and potassium sorbate.

In another embodiment of the present invention, the personal lubricant comprises a glow powder.

In one embodiment, the glow powder comprises a mixture of one or more glow components selected from $Al_2O_3$, $SrCO_3$, $Eu_2O_3$, $Dy_2O_3$ and $TiO_2$. In one embodiment, the glow powder comprises $Al_2O_3$, $SrCO_3$, $Eu_2O_3$, $Dy_2O_3$ and $TiO_2$. A nonlimiting example of this glow powder is lumoniva by Nemoto and Co.

In one embodiment the glow powder comprises zinc sulfide.

In one embodiment, the glow powder is included in the formula at about 2-5% by volume of the formula.

In addition to the glow powder, this personal lubricant may further comprise a carbomer.

Further, this lubricant embodiment may further comprise one or more additional components known by those of skill in the art to be useful in personal lubricants. For example, in one embodiment, the personal lubricant may further comprise a component which provides lubricity and/or serves as thickening agent. Examples include, but are not limited to carrageenan, glycerin, propylene glycol, polyquaternium, methylparaben, propylparaben, cellulose polymer, cyclomethicone, dimethicone, dimethiconol, petroleum based oils, plant based oils, as well as other substances that reduces the coefficient of friction or increases lubricity of the final formula, and mixtures thereof. In one embodiment, the component which provides lubricity and/or serves as a thickening agent is carrageenan. In addition to providing lubricity and serving as a thickening agent, carrageenan also has no taste, no smell, no color, allows for moisture retention, has pseudoplastic properties, acts as an emulsifier and has been shown to offer protection against human papillomavirus in previous clinical trials and may also offer some protection against HSV-2, the virus that causes herpes. In one embodiment, carrageenan is added in an amount of about 0.75% by volume to the formula. A nonlimiting example of a commercial supplier is Tedson Additive Inc.

In another embodiment, the personal lubricant may further comprise a thickening agent such as, but not limited to, a plant based gum. Hydroxyethyl cellulose gum is a nonlimiting example of a plant based gum which serves to thicken the formula and prevent separation of the various ingredients of the formula. In one embodiment, hydroethyl cellulose gum is added in an amount of about 0.7% by volume to the formula. A nonlimiting example of a commercial supplier is Tedson Additive Inc.

In another embodiment, the personal lubricant may further comprise a Lewis acid for adjustment of the pH. Examples include, but are not limited to, citric acid, phosphoric acid, hydrochloric acid, ascorbic acid, malic acid and lactic acid.

In another embodiment, the personal lubricant may further comprise an antiviral component such as L-lysine HCl. Viruses such as HSV are dependent on the presence of L-arginine, another amino acid, to replicate. By flooding the virus with L-lysine, the opposing amino acid, it helps to stop the replication of the virus. In one embodiment, the L-lysine HCL is included in the personal lubricant at a percentage of about 0.001% by volume of the formula.

In another embodiment, the personal lubricant may further comprise a preservative such as sodium benzoate or potassium benzoate. In one embodiment, the preservative is also bacteriostatic and fungistatic under acidic conditions. In one embodiment, the preservative is included in the personal lubricant at a percentage of about 0.01% or less by volume of the formula.

In yet another embodiment, the personal lubricant may further comprise an agent which inhibits molds and yeasts such as, but not limited to, potassium sorbate, sodium sorbate or xylitol. In one embodiment, the inhibitor of molds and yeasts is included in the personal lubricant at a percentage of about 0.05% to 0.3% by volume of the formula.

In one embodiment of the present invention, the personal lubricant comprises a glow powder, a carbomer, carrageenan, hydroxyethyl cellulose gum, citric acid, L-lysine HCl, sodium benzoate and potassium sorbate.

In yet another embodiment of the present invention, the personal lubricant comprises xylitol. In one embodiment, the xylitol is included in the personal lubricant at a percentage of about 2% by volume of the formula. Without being limited to a specific mechanism, it is believed that inclusion of xylitol in the personal lubricant formulation can inhibit and/or prevent yeast infections.

This xylitol containing lubricant embodiment may further comprise one or more additional components known by those of skill in the art to be useful in personal lubricants. For example, in one embodiment, the personal lubricant may further comprise a component which provides lubricity and/or serves as thickening agent. Examples include, but are not limited to carrageenan, glycerin, propylene glycol, polyquaternium, methylparaben, propylparaben, cellulose polymer, cyclomethicone, dimethicone, dimethiconol, petroleum based oils, plant based oils, as well as other substances that reduces the coefficient of friction or increases lubricity of the final formula, and mixtures thereof. In one embodiment, the component which provides lubricity and/or serves as a thickening agent is carrageenan. In addition to providing lubricity and serving as a thickening agent, carrageenan also has no taste, no smell, no color, allows for moisture retention, has pseudoplastic properties, acts as an emulsifier and has been shown to offer protection against human papillomavirus in previous clinical trials and may also offer some protection against HSV-2, the virus that causes herpes. In one embodiment, carrageenan is added in an amount of about 0.75% by volume to the formula. A nonlimiting example of a commercial supplier is Tedson Additive Inc.

In another embodiment, the xylitol containing personal lubricant may further comprise a thickening agent such as, but not limited to, a plant based gum. Hydroxyethyl cellulose gum is a nonlimiting example of a plant based gum which serves to thicken the formula and prevent separation of the various ingredients of the formula. In one embodiment, hydroethyl cellulose gum is added in an amount of about 0.7% by volume to the formula. A nonlimiting example of a commercial supplier is Tedson Additive Inc.

In another embodiment, the personal lubricant may further comprise a Lewis acid for adjustment of the pH. Examples include, but are not limited to, citric acid, phosphoric acid, hydrochloric acid, ascorbic acid, malic acid and lactic acid.

In another embodiment, the xylitol containing personal lubricant may further comprise an antiviral component such as L-lysine HCl. Viruses such as HSV are dependent on the presence of L-arginine, another amino acid, to replicate. By flooding the virus with L-lysine, the opposing amino acid, it helps to stop the replication of the virus. In one embodiment, the L-lysine HCL is included in the personal lubricant at a percentage of about 0.001% by volume of the formula.

In another embodiment, the xylitol personal lubricant may further comprise a preservative such as sodium benzoate or potassium benzoate. In one embodiment, the preservative is also bacteriostatic and fungistatic under acidic conditions. In one embodiment, the preservative is included in the personal lubricant at a percentage of about 0.01% or less by volume of the formula.

In yet another embodiment, the personal lubricant may further comprise an additional agent which inhibits molds and yeasts such as, but not limited to, potassium sorbate or sodium sorbate. In one embodiment, the inhibitor of molds and yeasts is included in the personal lubricant at a percentage of about 0.05% to 0.3% by volume of the formula.

In one embodiment of the present invention, the personal lubricant comprises xylitol, carrageenan, hydroxyethyl cellulose gum, citric acid, L-lysine HCl, sodium benzoate and potassium sorbate.

In one embodiment, the royal jelly, glow powder or xylitol containing personal lubricant further comprises docosanol or another antiviral agent effective against herpes simplex virus. In this embodiment, the antiviral agent is included in an amount effective to inhibit or reduce duration of a viral outbreak.

As will be understood by the skilled artisan upon reading this disclosure, additional components routinely included in personal lubricants can also be added. Addition of such components is encompassed within the scope of the instant invention.

The following nonlimiting examples are provided to further illustrate the present invention. These examples are illustrative only and are not intended to limit the scope of the invention in any way.

EXAMPLES

Example 1: Personal Lubricant Containing Royal Jelly

The following ingredients are provided in quantities to be admixed to produce a final composition having the ingredients in the weight percent noted:
Carrageenan 0.75%
Hydroxyethyl Cellulose 0.7%
Sodium Lactate 0.5%
Propylene Glycol 2.0%
Royal Jelly 0.001%
L-Lysine 0.001%
Sodium benzoate 0.01%
Potassium Sorbate 0.05%
Citric acid 1.0%
Purified water 95%

These ingredients are then mixed as follows. The water is metered into a first mixing vessel, and agitation is engaged. The potassium sorbate, sodium benzoate, citric acid, L-lysine, royal jelly, sodium lactate, and hydroxyethyl cellulose are added to the water and mixed to uniformity. In a second mixing vessel the propylene glycol and carrageenan are mixed together to uniformity and are then admixed to the composition in the first mixing vessel. At this time further additives, medicaments, ingredients, etc. may be added and blended to uniformity.

The process can be carried out by a batch process, a continuous process or a combination of the two. The resulting lubricant composition may be scented or unscented, colored or colorless, flavored or flavorless, water-based, and/or may include humectants. The formula is pH balance with a range between 3.7 and 4.3, currently preferably 4.0.

Example 2: Personal Lubricant Containing Glow Powder

The following ingredients are provided in quantities to be admixed to produce a final composition having the ingredients in the weight percent noted:
Carrageenan 0.75%
Hydroxyethyl Cellulose 0.7%
Sodium Lactate 0.5%
Propylene Glycol 2.0%
L-Lysine 0.001%
Sodium benzoate 0.01%
Potassium Sorbate 0.05%
Citric acid 1.0%
Glow powder 5%
Carbomer 5%
Purified water 85%

These ingredients are then mixed as follows. The water is metered into a first mixing vessel, and agitation is engaged. The potassium sorbate, sodium benzoate, citric acid, L-lysine, sodium lactate, glow powder, carbomer, and hydroxyethyl cellulose are added to the water and mixed to uniformity. In a second mixing vessel, the propylene glycol and carrageenan are mixed together to uniformity and are then admixed to the composition in the first mixing vessel. At this time further additives, medicaments, ingredients, etc. may be added and blended to uniformity.

The process can be carried out by a batch process, a continuous process or a combination of the two. The resulting lubricant composition may be scented or unscented, colored or colorless, flavored or flavorless, water-based, and/or may include humectants. The formula is pH balance with a range between 3.7 and 4.3, currently preferably 4.0.

Example 3: Personal Lubricant Containing Xylitol

The following ingredients are provided in quantities to be admixed to produce a final composition having the ingredients in the weight percent noted:
Carrageenan 0.75%
Hydroxyethyl Cellulose 0.7%
Sodium Lactate 0.5%
Propylene Glycol 2.0%
Xylitol 2%
L-Lysine 0.001%
Sodium benzoate 0.01%
Potassium Sorbate 0.05%
Citric acid 1.0%
Purified water 93%

These ingredients are then mixed as follows. The water is metered into a first mixing vessel, and agitation is engaged. The potassium sorbate, sodium benzoate, citric acid, L-lysine, xylitol, sodium lactate, and hydroxyethyl cellulose are added to the water and mixed to uniformity. In a second mixing vessel the propylene glycol and carrageenan are mixed together to uniformity and are then admixed to the composition in the first mixing vessel. At this time further additives, medicaments, ingredients, etc. may be added and blended to uniformity.

The process can be carried out by a batch process, a continuous process or a combination of the two. The resulting lubricant composition may be scented or unscented, colored or colorless, flavored or flavorless, water-based, and/or may include humectants. The formula is pH balance with a range between 3.7 and 4.3, currently preferably 4.0.

What is claimed is:

1. A personal lubricant comprising from 0.05 to 2% by volume of xylitol, a component which provides lubricity, hydroxyethyl cellulose, 0.001% by volume of L-lysine HCl, a preservative and 85 to 95% by volume of purified water.

2. The personal lubricant of claim 1 wherein the component is selected from the group consisting of carrageenan, glycerin, propylene glycol, polyquaternium, methylparaben, propylparaben, cellulose polymer, cyclomethicone, dimethicone, dimethiconol, petroleum based oils, plant based oils, as well as other substances that reduces the coefficient of friction or increases lubricity of the final formula, and mixtures thereof.

3. The personal lubricant of claim 1 further comprising a Lewis acid.

4. The personal lubricant of claim 1 further comprising an antiviral agent.

5. The personal lubricant of claim 4 wherein the antiviral agent is effective against herpes simplex virus.

* * * * *